US007067811B2

(12) United States Patent
Long et al.

(10) Patent No.: US 7,067,811 B2
(45) Date of Patent: Jun. 27, 2006

(54) NIR SPECTROSCOPY METHOD FOR ANALYZING CHEMICAL PROCESS COMPONENTS

(75) Inventors: Yicheng Long, Edmonton (CA); Tadeusz Dabros, Edmonton (CA); Hassan Hamza, Edmonton (CA)

(73) Assignee: Her Majesty the Queen in right of Canada, as represented by the Minister of Natural Resources Canada, Ottawa (CA)

( * ) Notice: Subject to any disclaimer, the term of this patent is extended or adjusted under 35 U.S.C. 154(b) by 223 days.

(21) Appl. No.: 10/686,725

(22) Filed: Oct. 17, 2003

(65) Prior Publication Data

US 2004/0084623 A1 May 6, 2004

Related U.S. Application Data

(60) Provisional application No. 60/423,975, filed on Nov. 6, 2002.

(51) Int. Cl.
*G01N 21/33* (2006.01)
*G01J 5/02* (2006.01)

(52) U.S. Cl. .............................. 250/339.12; 250/339.09
(58) Field of Classification Search ........... 250/339.12, 250/339.09, 269.1
See application file for complete search history.

(56) References Cited

U.S. PATENT DOCUMENTS

| 4,843,247 | A | | 6/1989 | Yamazoe et al. ............ 250/573 |
|---|---|---|---|---|
| 4,866,983 | A | * | 9/1989 | Vinegar et al. ............ 73/152.09 |
| 5,532,487 | A | | 7/1996 | Brearley et al. ......... 250/339.12 |
| 5,672,873 | A | | 9/1997 | Yamazoe ................. 250/339.12 |
| 5,712,165 | A | * | 1/1998 | Alvarez et al. ................ 436/21 |
| 5,742,064 | A | | 4/1998 | Infante ...................... 250/458.1 |
| 6,087,662 | A | * | 7/2000 | Wilt et al. .............. 250/339.12 |
| 6,281,489 | B1 | * | 8/2001 | Tubel et al. ............ 250/227.14 |
| 6,300,633 | B1 | | 10/2001 | Hunt et al. ............. 250/339.12 |
| 6,507,401 | B1 | * | 1/2003 | Turner et al. ................ 356/436 |
| 2002/0139929 | A1 | * | 10/2002 | Mullins et al. .............. 250/255 |

FOREIGN PATENT DOCUMENTS

WO WO 97/14953 4/1997

\* cited by examiner

*Primary Examiner*—David P. Porta
*Assistant Examiner*—Christopher Webb (57) ABSTRACT

A method is described for providing rapid on-line analyses of chemical compositions such as chemical process streams, utilizing near-infrared (NIR) spectroscopy in combination with chemometrics. In the method, for each type of analysis to be conducted, a database is provided by analyzing a series of samples using standard laboratory analytical procedures, utilizing the results as reference values to establish quantitative calibration models from NIR spectroscopy using chemometric techniques and storing this information in a computer database. An NIR spectroscopic system is also provided comprising a transflectance or a transmittance probe coupled via fiber-optic cables to a stable white light source and a spectrograph. The probe is inserted into a test sample or chemical process stream to be analyzed, a stable white light of selected wavelength range is beamed to the probe and the spectra obtained on the spectrograph are recorded. Finally the spectra obtained are correlated to the reference data stored in the computer to obtain a rapid measurement of the analysis desired.

13 Claims, 5 Drawing Sheets

NIR SPECTROSCOPY METHOD FOR ANALYZING CHEMICAL PROCESS COMPONENTS

CROSS-REFERENCE TO RELATED APPLICATION

This application claims the benefit of Provisional Application Ser. No. 60/423,975, filed Nov. 6, 2002.

BACKGROUND OF THE INVENTION

This invention relates to a NIR spectroscopy method for analysis of chemical process components, e.g. for analysis of bitumen and solvent-diluted bitumen from froth treatment during oil sands processing.

In analytical or research activities, as well as in industrial chemical processes, there is a need for highly reliable real or near real time analysis of chemical components, e.g. for froth treatment during oil sands processing. In the extraction of bitumen from oil sands, froth treatment is an essential step for removing water and solids from bitumen froth to produce bitumen meeting product specifications. The bitumen froth usually contains about 60 wt % bitumen, 30 wt % water, and 10 wt % solids. Current commercial froth treatment employs naphtha dilution followed by multistage centrifugation, which gives a diluted bitumen product typically containing about 0.3 to 1.0 wt % solids and about 1 to 5 wt % water. An alternative froth treatment process uses aliphatic solvent as froth diluent. A diluted bitumen product that contains less than 0.1 wt % water and solids and controlled levels of asphaltenes can be produced. It has previously been shown that, the performance of the froth treatment process using aliphatic solvent depends greatly on controlling process parameters; among the most important of these are the solvent-to-bitumen ratio (S/B, by wt), asphaltenes rejection level, and density of the solvent-diluted bitumen oil phase. Successful control of these process parameters ensures the desired level of asphaltenes in product, sufficient settling flux of water and solids, and on-spec product (e.g., containing less than 0.1 wt % water plus solids).

At present, the S/B of solvent-diluted bitumen is determined by vacuum rotary evaporation (Rotavapor), the asphaltenes content of bitumen is analyzed using the standard ASTM or IP methods that are based on precipitation of asphaltenes by light aliphatic solvent and followed filtration, and the density of solvent-diluted bitumen is measured using a laboratory density meter. These analyses are labor-intensive and time-consuming. Rotavapor takes approximately 1.5 h to complete and asphaltenes content analysis takes about 6 h. Furthermore, the accuracy of the analytical results depends on the skill of the analyst. Consistency of the results from various laboratories is frequently not satisfactory. Therefore, more reliable and faster analytical methods are required to better monitor performance and to permit timely adjustments of the operating conditions of the froth treatment process.

Near-infrared spectroscopy (NIR) provides information on chemical and physical properties of sample components. Chemometric methods based on eigenvalue decomposition of a data matrix are effective tools for analyzing correlations between spectral information and compositions and properties. Principal component analysis (PCA) and partial least squares in latent variables (PLS) are commonly used techniques. NIR in combination with chemometrics is hence a powerful approach for fast routine and on-line chemical analyses.

U.S. Pat. No. 5,742,064, issued Apr. 21, 1998, describes a system for detecting water and dirt in petroleum flowing through a pipeline. Light is projected into the petroleum and light which is not absorbed by impurities contained in the petroleum is transmitted to a photomultiplier or spectrometer. Three different optical waveguides are used and the light source is a tunable laser.

A method for measuring asphaltene concentration of hydrocarbon feedstocks using spectroscopy is described in U.S. Pat. No. 6,087,662, issued Jul. 11, 2000. IR spectroscopy is used in mid-range IR frequencies between about 3800 $cm^{-1}$ and 650 $cm^{-1}$. This uses an ATR and a photomultiplier. It has an absolute accuracy of about 0.9–1.3% for asphaltenes contents below 4%.

Heint et al., U.S. Pat. No. 6,300,633, issued Oct. 9, 2001, describes an in-line spectrometric method for determining the residue content of an isocyanate. It uses a probe capable of directing light at wavelengths of from 1050 to 2150 nm into a process stream. A near-infrared spectrum is generated and the residue content is determined using a chemometric model.

It is an object of the present invention to provide a method for using NIR spectroscopy for analysis of bitumen and solvent-diluted bitumen samples from the bitumen froth treatment process, that can be used for fast routine and on-line analysis.

SUMMARY OF THE INVENTION

This invention relates to the use of NIR spectroscopy for the analysis of chemical compositions, and particularly for the near real time analysis of chemical process components during continuous processing.

For each component to be analyzed, a series of analyses are carried out using standard analytical procedures and these results are used as reference values for establishing and evaluating quantitative calibration models from NIR spectroscopy. The NIR spectra are correlated to the reference analytical data using chemometric techniques, e.g. methods based on eigenvalue decomposition of a data matrix. Techniques that may be used include principal component analysis (PCA) and partial least squares in latent variables (PLS).

In order to achieve accurate results from NIR spectroscopy the NIR hardware must exhibit long-term stability. This includes stability of the light source, detector, electronics and mechanical systems. To achieve this stability, an NIR system is used comprising a double-pass transflectance probe coupled via fiber-optic cables to a stable white light source and a spectrograph. It is also advantageous to use a spectrograph with no moving parts and a probe with a long light path to minimize some secondary temperature effects. The probe is inserted into a material to be analyzed and a beam of stable white light is directed into the probe. The spectra obtained are recorded in the spectrograph and correlated to stored analytical data to provide a direct measurement of the feature of the material being analyzed. In this manner, the amounts of particular components in the material being analyzed may be determined, as well as other characteristics of the material, such as density, etc.

In a preferred embodiment, NIR spectroscopy according to this invention is used in process control and optimization of bitumen froth treatment during oil sands processing. The NIR spectroscopy according to this invention provides the necessary rapid analysis of the asphaltenes content in the bitumen product, as well as the solvent-to-bitumen ratio, and the density of the solvent-diluted product.

During the extraction of bitumen from oil sands, a froth is formed and the froth is treated to remove water and solids to produce a clean bitumen. The treatment of the froth includes a first dilution stage in which the froth is diluted with an aliphatic solvent before conducting steps to remove water and solids and thus obtain a clean bitumen product. An NIR spectroscopic system is provided comprising a double-pass transflectance probe coupled via fiber-optic cables to a stable white light source and a spectrograph. The probe is inserted in a bitumen or solvent-diluted bitumen sample generated from the bitumen froth treatment and a beam of stable white light is directed into the probe. The spectra obtained are recorded in the spectrograph. These spectra are compared with stored reference data for one or more of (a) asphaltenes content in the bitumen product, (b) solvent-to-bitumen ratio of a solvent-diluted bitumen and (c) density of a solvent-diluted bitumen, to provide direct values of each. The white light preferably has a wavelength in the range 900 to 1700 nm and a light pass length in the range of 0.1 to 20 mm, preferably 1 to 10 mm, is used.

With the system of this invention, the system is trained with respect to the particular tests being conducted. If it encounters an analysis situation for which the system has not been trained, a signal is given.

DESCRIPTION OF THE PREFERRED EMBODIMENTS

Figure 1:
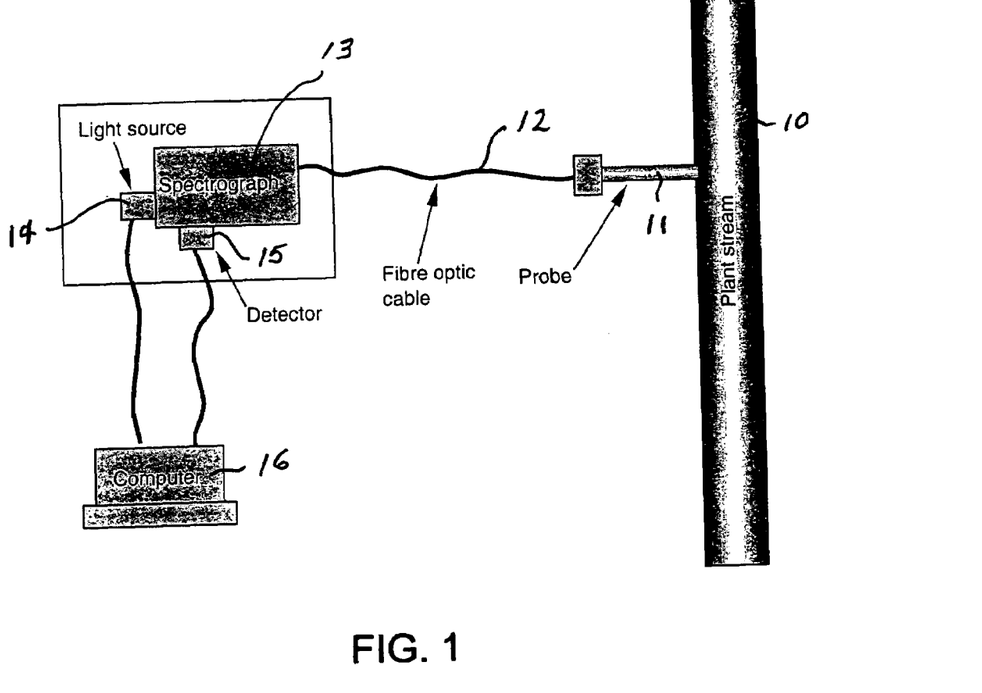
FIG. 1 is a schematic illustration of an NIR spectroscopy arrangement according to the invention.

A schematic illustration of the NIR spectroscopy system for carrying out the invention is shown in FIG. 1. The material to be analyzed is carried in plant line 10 and a double-pass transflectance probe 11 extends through an opening into line 10. The probe 11 is coupled with a stable light source 14 an array detector 15 and a spectrograph 13 with no moving parts by way of fiber-optic cables 12. The computer 16 holds stored reference data and the recorded spectra are compared to the stored reference data to simply compute a direct value for the particular analysis being carried out.

The froth treatment process using aliphatic solvent produces a clean solvent-diluted bitumen product and a sediment phase containing mainly water, solids, and precipitated asphaltenes. Solvent-diluted bitumen samples from both batch and continuous pilot tests were used in a test program. The batch test procedure was described in Long Y, Dabros T, Hamza H, "Stability and settling characteristics of solvent-diluted bitumen emulsions", Fuel, 2002;81(15):1945–52, incorporated herein by reference. The pilot operation was performed in a froth treatment pilot plant, at CANMET Energy Technology Centre—Devon, Alberta. A mixture of pentane and hexane was used as solvent for all tests. Bitumen from the solvent-diluted bitumen product was recovered by removing solvent using a Rotavapor (vacuum rotary evaporator). This bitumen contained 0 to 20 wt % asphaltenes. Bitumen from the froth treatment sediment phase was also recovered by extraction with toluene following rotary evaporation of the toluene-diluted bitumen solution. The bitumen from the sediment phase contained 20 to 100 wt % asphaltenes.

EXAMPLE 1

Tests were conducted using the NIR spectrograph arrangement shown in FIG. 1. It comprised a spectrograph that had no moving parts, a linear array detector, a stable light source, and a double-pass transflectance probe with fiber-optic cable coupling the light source and the spectrograph. The wavelength range was 900 to 1700 nm.

Sample spectra were recorded by directly dipping the transflectance probe into sample solutions. The solvent-diluted bitumen samples were measured directly with a 2-mm light path length probe without further dilution. The bitumen, asphaltenes, and maltenes samples were diluted with solvent (toluene or $CS_2$) and the measurement was done with a 10-mm light pass length probe.

All samples were analyzed using standard laboratory analytical procedures. The results were used as reference values for establishing and evaluating the quantitative calibration models from NIR.

The n-C5 asphaltenes content in bitumen was determined by following the test methods ASTM D 3297-97, 1997 and IP 143–96, 1996. S/B of solvent-diluted bitumen was obtained by removing solvent using the Rotavapor. Density of solvent-diluted bitumen was measured at 25° C. using an Anton Paar density meter (model DMA 4500).

The NIR spectra were correlated to the reference analytical data using chemometric techniques. The calibration models were established using PLS. Eigenvectors were found to most efficiently span the data points and the maximized linear regression fit was then obtained between data scaling factors (scores). Sample classification was examined using PCA scores. The singular value decomposition (SVD) algorithm was used. The optimal rank was determined by evaluating the reduced eigenvalues of the eigenvectors. The calibration models were validated either by using the "leave-one-out cross validation" method or by using an independent validation data set. The standard error of calibration (SEC) was calculated when the leave-one-out cross validation method was used and the standard error of validation (SEV) was calculated when an independent validation data set was used:

$$SEC \text{ (or } SEV\text{)} = \sqrt{\frac{\sum\limits_{i=1}^{i=n}(y_P - y_R)^2}{n}}$$

where n is the number of data points; $y_P$ is the predicted result according to the model; $y_R$ is the reference analytical result.

The absorption bands of organic compounds in NIR region are the molecular vibrational transition (mainly due to the C—H, N—H, and O—H bonds) overtones and combinations. Table 1 lists the C—H absorptions and relative absorption intensities. In general, the higher the overtone order, the lower the absorption intensity. Therefore, the higher-order overtone bands should be used if a longer light path length for recording spectra is preferred for easier sample preparation and higher signal reproducibility. In this work, the second-order overtone and combination bands (1000 to 1600 nm) were used.

TABLE 1

NIR absorption bands of C—H bond

| Absorption band | Wavelength (nm) | Relative intensity |
|---|---|---|
| Fundamental band | 3380–3510 | 1 |
| First-order overtone | 1690–1755 | 0.01 |
| Second-order overtone | 1125–1225 | 0.001 |
| Third-order overtone | 845–878 | 0.0001 |

Figure 2:
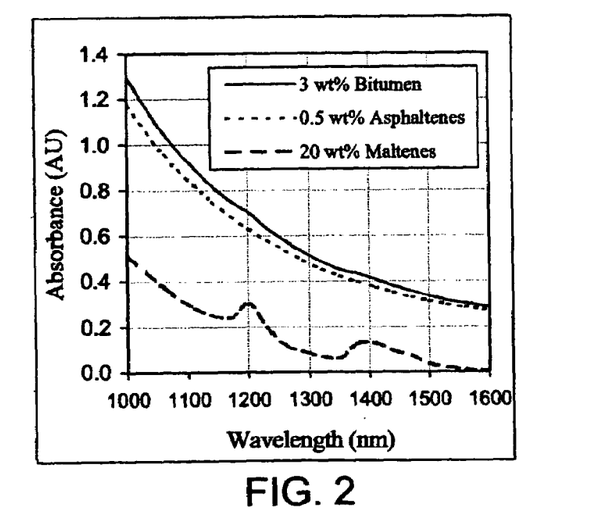
FIG. 2 shows NIR spectra of bitumen, maltenes and asphaltenes.

FIG. 2 shows the representative NIR spectra for oil sands bitumen (3 wt % solution in $CS_2$), asphaltenes (0.2 wt % solution in $CS_2$), and maltenes (20 wt % solution in $CS_2$) from 1000 to 1600 nm. The maltenes spectrum clearly shows the second-order C—H overtone features at around 1200 nm and the combination band at around 1400 nm. The asphaltenes spectrum shows only a broad band across the whole spectral range without significant C—H overtone peaks. The light absorption of the asphaltenes was much stronger than that of the maltenes. The Athabasca oil sands bitumen contained 17.5 wt % asphaltenes and the rest was maltenes. The bitumen spectrum feature was dominated by asphaltenes absorption characteristics and the bitumen and asphaltenes spectra were very similar.

Asphaltenes are the heaviest bitumen fraction with condensed aromatic-ring structures. It is believed that they stay in solution as a colloidal dispersion. Therefore, the apparent NIR absorption of asphaltenes can arise from both electronic transition of the condensed-aromatic structure and light scattering by the colloidal asphaltenes particles. It is of interest in this work to know which mechanism dominates, as light absorbance due to electronic transition usually has a good linear relationship with concentration; on the other hand, the light scattering intensity of asphaltenes is expected to depend on many conditions such as solvent type and solvent dilution ratio. A prior study has been made of the NIR absorption of crude oil asphaltenes in $CCl_4$ solution with a wide range of solvent dilution ratios, and the conclusion was reached that the dominant light attenuation mechanism of the asphaltenes in crude oils is absorption, not scattering.

EXAMPLE 2

Figure 3:
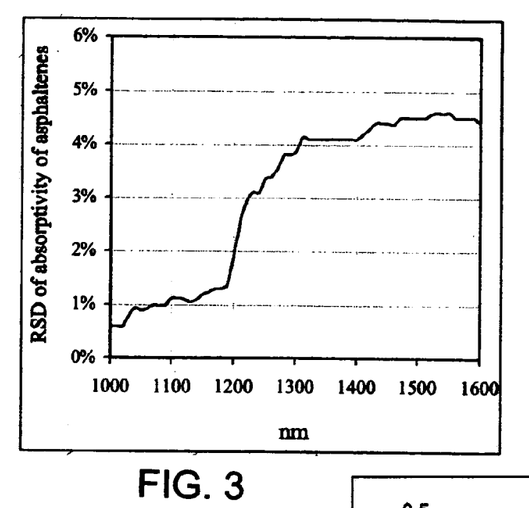
FIG. 3 is a graph showing relative standard deviation of asphaltene absorptivity in various asphaltene-toluene concentrations.

A series of asphaltenes-toluene solutions were prepared with various asphaltenes concentrations (0.08, 0.13, 0.22, 0.44, and 0.87 g/100 mL). NIR spectra of these samples and pure toluene were recorded using a 10-mm light path length transflectance probe. The contribution of toluene to the absorbance was subtracted by calculating the difference of the sample solution spectra and the pure toluene spectrum (considering the dilution factor). Absorptivities of asphaltenes were calculated as:

$$K_i = \frac{A_i}{L \times C}$$

where $K_i$ is the absorptivity of asphaltenes at wavelength i, $A_i$ is the absorbance of the asphaltenes solution (subtracted toluene) at wavelength i, L is the light path length in centimeters, C is the asphaltenes concentration in grams of asphaltenes per 100 mL solution. The relative standard deviation (RSD) of Ki within the six asphaltenes solutions was then calculated. FIG. 3 shows the variation of Ki, in response to solvent dilution changes, as a function of wavelength. The RSD was less than 1.0% at wavelengths from 1000 to 1100 nm and about 1% to 5% at wavelengths from 1100 to 1600 nm. This indicates that the light attenuation of asphaltenes obeys the Beer-Lambert law and is likely dominated by light absorption due to electronic transition, especially in the region of 1000 to 1100 nm.

EXAMPLE 3

Figure 4:
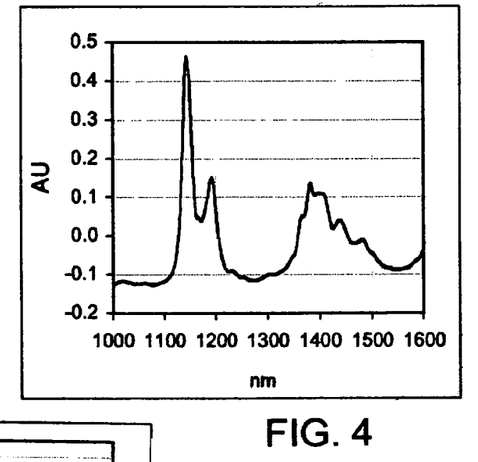
FIG. 4 shows forty toluene spectra recorded over a period of two weeks.
Figure 5:
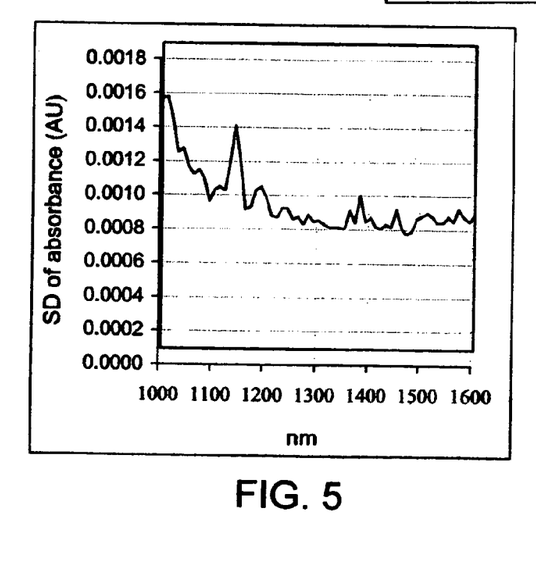
FIG. 5 is a graph showing standard deviation of absorbance for the forty spectra of FIG. 4.

The long-term stability of the NIR system is essential for the successful use of the instrument as an analytical tool. Several previous attempts to use spectroscopy to measure similar properties failed because lack of stability. FIG. 4 shows 40 toluene spectra acquired during a period of two weeks (4 spectra per day). High spectral reproducibility is clearly evident. The standard deviation (SD) of absorbance is presented in FIG. 5. An SD of less than 0.0015 absorbance units (AU) was observed. The RSD for the toluene peak at 1145 nm was 0.2%. The high reproducibility of the NIR system is believed to be due mainly to the highly stable spectrograph and the array detector, which have no moving parts, and the long light path length (10 mm) that prevents sample temperature variation during spectrum acquisition. The original spectra were therefore used directly for establishing calibration models.

EXAMPLE 4

Studies were conducted on the analysis of asphaltenes contents in bitumen and predicted and reference asphaltene contents were compared. Two calibration models were established: one for the bitumen samples containing 0 to 20 wt % asphaltenes and the other for bitumen samples containing 20 to 100 wt % asphaltenes. The former were samples that originated from the solvent-diluted bitumen product during froth treatment; the latter were samples from the froth treatment sediment phase. During spectroscopic analysis of the bitumen samples, a toluene-to-bitumen dilution ratio of 20 (by wt) was used for the samples containing less than 20 wt % asphaltenes and a ratio of 120 was used for the samples containing more than 20 wt % asphaltenes.

Figure 6:
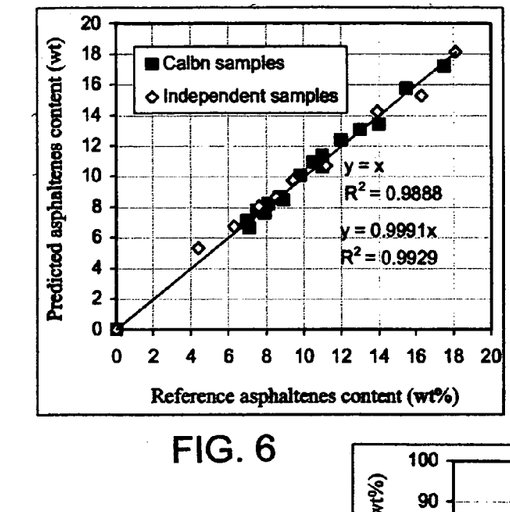
FIG. 6 is a graph comparing predicted asphaltene content with actual analytical results for 0 to 20 wt % asphaltenes content.

The optimized wavelength range for predicting asphaltenes content was found to be 1000 to 1100 nm, which is consistent with the results of FIG. 3. FIG. 6 presents the prediction results for 0 to 20 wt % asphaltenes content. Two PLS components were used for the model. Excellent agreement was found between the predicted data and the actual analytical results. SEC and SEV were 0.20 wt % and 0.23 wt %, respectively.

Figure 7:
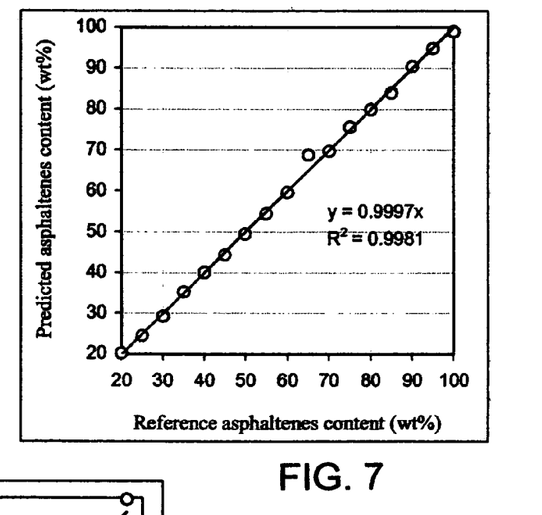
FIG. 7 is a graph comparing predicted asphaltene content with actual analytical results for 20 to 100 wt % asphaltene content.

FIG. 7 shows the prediction results for 20 to 100 wt % asphaltenes content. The model used two PLS components and exhibited an SEC of 1.1 wt %.

EXAMPLE 5

This is a study on determining the density of solvent-diluted bitumen.

Figure 8:
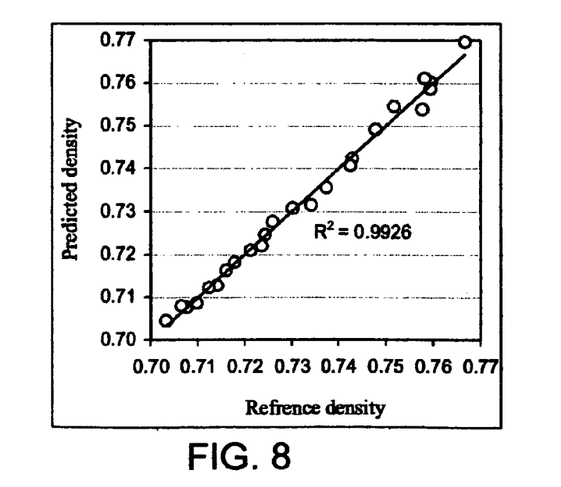
FIG. 8 is a graph showing the predicted density of solvent-diluted bitumen solution vs the value determined using a density meter.

The wavelength range of 1000 to 1600 nm was used. FIG. 8 shows the predicted density of solvent-diluted bitumen solution vs. the value determined using density meter. Three PLS components were used to establish the calibration model and an SEC of 0.0017 g/mL was obtained.

EXAMPLE 6

This example is a study on determining the solvent-to-bitumen ratio (S/B) of solvent-diluted bitumen.

Figure 9:
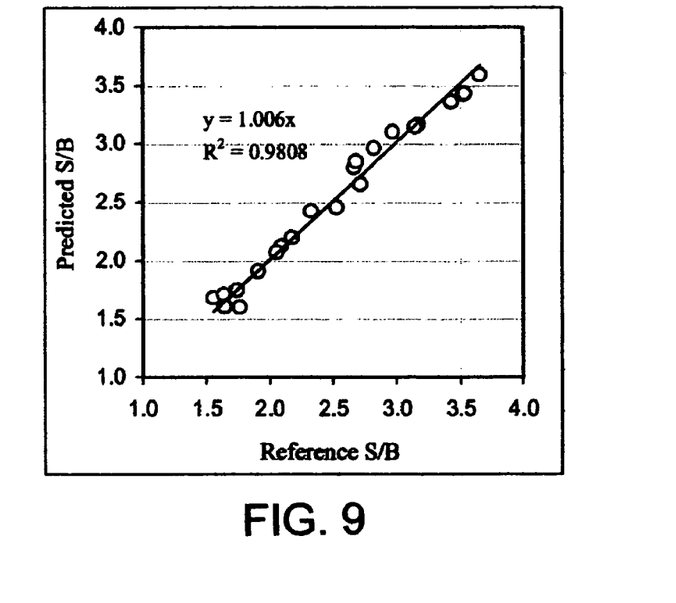
FIG. 9 is a graph showing the predicted S/B of solvent-diluted bitumen solution vs the reference S/B.

S/B is one of the most important operating parameters to be monitored and controlled in commercial froth treatment. It affects product quality (water content, solids content, asphaltenes rejection level), bitumen recovery, and the settling rates of water and solids. FIG. 9 shows the results of S/B predictions using NIR. The wavelength range from 1040 to 1600 nm was used and three PLS components were sufficient to generate a reliable calibration model. An SEC of 0.1 was obtained.

Figure 10:
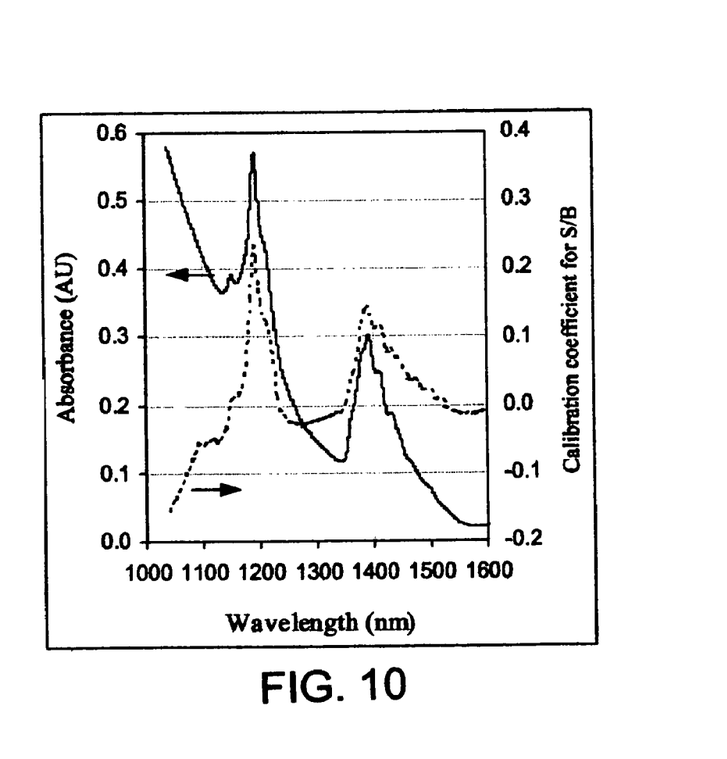
FIG. 10 is a typical NIR spectrum of a solvent-diluted bitumen sample and the PLS calibration coefficient for S/B.

FIG. 10 shows a typical NIR spectrum of a solvent-diluted bitumen sample and the PLS calibration coefficient for S/B. The 1040 to 1150 nm wavelength range was taken as negatively correlated to S/B, as light absorption in this range was dominated by bitumen. The absorptions at around 1200 nm and 1400 nm were characteristic of hydrocarbon solvent, and were positively correlated to S/B.

EXAMPLE 7

Figure 11:
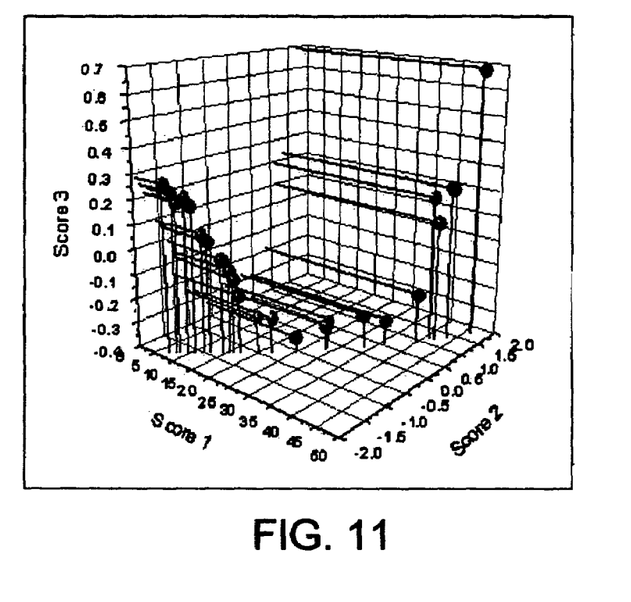
FIG. 11 is a three dimensional representation of the first three PCA spectral scores of diluted bitumen spectra.

This example relates to principal component analysis of NIR spectra of solvent-diluted bitumen. During froth treatment, process conditions fluctuate and result in variations in product quality. FIG. 11 shows the first three PCA spectral scores of the clean diluted bitumen samples (containing less than 0.1 wt % water plus solids). The data points were located along a U-shaped corridor. The left-hand side of the graph is the region of high S/B (starting from 4.0), low density, and high asphaltenes content; the right-hand side is the region of low S/B (starting from 1.5), high density, and high asphaltenes content. When the S/B of the diluted bitumen sample was gradually reduced from 4.0 to 1.5, the data point would slide to the valley from the left-hand side, and then climb up to the right-hand side. A similar real-time display of PCA spectral scores during commercial operation would be an effective way of monitoring process performance and product quality.

Figure 12:
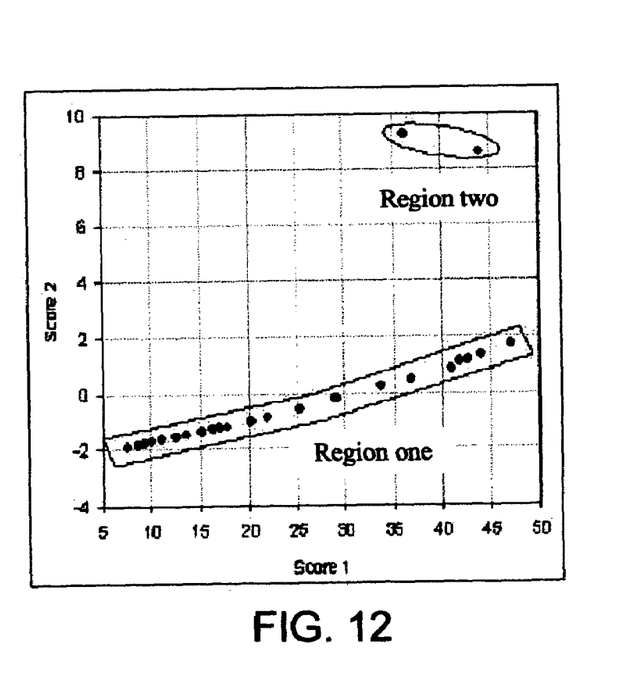
FIG. 12 is a two dimensional map showing the first two PCA spectral scores.

FIG. 12 is a 2-D map showing the first two PCA spectral scores. Region one is the clean product region. The solvent-diluted bitumen products are clean (containing less than 0.1 wt % water and solids) as long as the data point remains confined to this region. Region two is the region of contaminated solvent-diluted bitumen, i.e., water content=1 to 6 wt % and solids content=0.5 to 3 wt %. During process monitoring, the data point will jump from Region one to Region two if process upset occurs. The time that is needed for a data point to move from one region to the other is an indication of the system response time (or residence time).

In the above tests, the standard deviation of absorbance over a two-week period was less than 0.0015 AU. Due to the high stability of the instrument, the original spectra were used directly instead of the first- or the second-order derivatives. The PLS with the SVD algorithm was used to establish the calibration models. The PCA scores of the spectra were used for sample classification. The method was successfully used for predicting asphaltenes content (0 to 100 wt %) in bitumen and the S/B and density of solvent-diluted bitumen. Table 2 summarizes the results. The method is suitable for fast routine analysis and for on-line process applications.

TABLE 2

NIR analytical results for oil sands bitumen and solvent-diluted bitumen

| Parameter to be predicted | Wavelength range used | Number of PLS components used | SEC | SEV |
|---|---|---|---|---|
| Asphaltenes content in bitumen (0–20 wt %) | 1000–1100 nm | 2 | 0.20 wt % | 0.23 wt % |
| Asphaltenes content in bitumen (20–100 wt %) | 1000–1100 nm | 2 | 1.1 wt % | |
| S/B of solvent-diluted bitumen | 1040–1600 nm | 3 | 0.1 | |
| Density of solvent-diluted bitumen at 25° C. | 1000–1600 nm | 3 | 0.0017 g/ml | |

The method of this invention when used for the analysis of bitumen streams given exceptionally accurate results. Thus, it gives an absolute accuracy of 0.2 wt % or better for 0 to 20 wt % asphaltenes content streams, 1.1 wt % or better for higher than 20 wt % asphaltenes content streams, absolute error of 0.1 or better for measurement of solvent-to-bitumen ratio and absolute error 0.0017 g/ml or better for measurement of the density of solvent-diluted bitumen.

The invention claimed is:

1. A method for providing rapid on-line analyses of bitumen compositions for determining asphaltenes content thereof or for determining solvent-to-bitumen ratio or density of solvent diluted bitumen utilizing near-infrared (NIR) spectroscopy in combination with chemometrics which comprises:

(a) for each type of analysis to be conducted, providing a database by analyzing a series of samples using standard laboratory analytical procedures, utilizing the results as reference values to establish quantitative calibration models from NIR spectroscopy using chemometric techniques and storing this information in a computer database, (b) providing an NIR spectroscopic system comprising a double-pass, transflectance probe having a long light path, coupled via fiber-optic cables to a stable white light source and a spectrograph, (c) inserting said probe into a chemical composition to be analyzed and beaming to said probe a stable white light of selected wavelength range and recording the spectra obtained on the spectrograph, and (d) correlating the spectra obtained to the reference data stored in the computer to obtain a rapid measurement of the analysis desired.

2. The method of claim 1 wherein said chemometric techniques are based on eigenvalue decomposition of a data matrix.

3. The method of claim 2 wherein the eigenvalue decomposition determinations utilized principal component analysis (PCA) and partial least squares in latent variables (PLS).

4. The method of claim 2 wherein the bitumen composition is a solvent diluted froth stream obtained in the extraction of bitumen ftom oil sands.

5. The method of claim 4 wherein the asphaltenes content of the stream is determined.

6. The method of claim 4 wherein the solvent-to-bitumen ratio of the stream is determined.

7. The method of claim 4 wherein the density of the stream is determined.

8. The method of claim 4 wherein a stable white light of wavelength in the range 900 to 1700 nm is used.

9. The method of claim 5 wherein a stable white light of wavelength in the range 1000 to 1100 nm is used.

10. The method of claim 6 wherein a stable white light of wavelength in the range 1040 to 1600 nm is used.

11. The method of claim 7 wherein a stable white light of wavelength in the range 1000 to 1600 nm is used.

12. The method of claim 8 wherein a light pass length in the range of 0.1 to 20 mm is used.

13. The method of claim 1 wherein the NIR spectroscopy system used is highly stable and free of any moving parts.

* * * * *